United States Patent [19]

Preikschat

[11] Patent Number: 5,684,247
[45] Date of Patent: Nov. 4, 1997

[54] ROTATING CONSISTENCY TRANSMITTER IMPELLER AND METHOD

[75] Inventor: Ekhard Preikschat, Bellevue, Wash.

[73] Assignee: APPA System, Inc., Bellevue, Wash.

[21] Appl. No.: 666,903

[22] Filed: Jun. 19, 1996

Related U.S. Application Data

[63] Continuation-in-part of Ser. No. 525,945, Sep. 8, 1995, Pat. No. 5,600,058, and Ser. No. 624,982, Mar. 29, 1996.

[51] Int. Cl.$^6$ .................................................. G01N 11/14
[52] U.S. Cl. .................................... 73/54.32; 73/53.03
[58] Field of Search .................................. 73/54.23, 54.28, 73/54.31, 54.32, 54.33, 54.34, 54.35

[56] References Cited

U.S. PATENT DOCUMENTS

| | | | |
|---|---|---|---|
| 3,181,349 | 5/1965 | Jansson | 73/54.28 X |
| 3,572,086 | 3/1971 | Johnston | 73/54.32 |
| 4,062,226 | 12/1977 | Hietala | 73/54.23 |
| 4,077,251 | 3/1978 | Winter | 73/54.35 |
| 4,175,425 | 11/1979 | Brookfield | 73/54.28 |
| 4,878,378 | 11/1989 | Harada | 73/54.35 |
| 5,349,848 | 9/1994 | Driver | 73/54.28 |
| 5,357,785 | 10/1994 | Hemmings et al. | 73/54.32 |

FOREIGN PATENT DOCUMENTS

| | | | |
|---|---|---|---|
| 0303708 | 2/1955 | Switzerland | 73/54.23 |

*Primary Examiner*—Michael Brock
*Attorney, Agent, or Firm*—Dean A. Craine

[57] ABSTRACT

An improved impeller for a rotating consistency transmitter and a method of measuring the consistency of pulp slurry flowing in a main pipeline. The impeller includes an intercepting surface designed to minimize the creation of turbulence in pulp slurry and the frictional forces on the front edge thereof when rotated in the pulp slurry. Using the impeller, a method of measuring the consistency of the pulp slurry is provided which measures the work done by forces acting on the impeller.

5 Claims, 8 Drawing Sheets

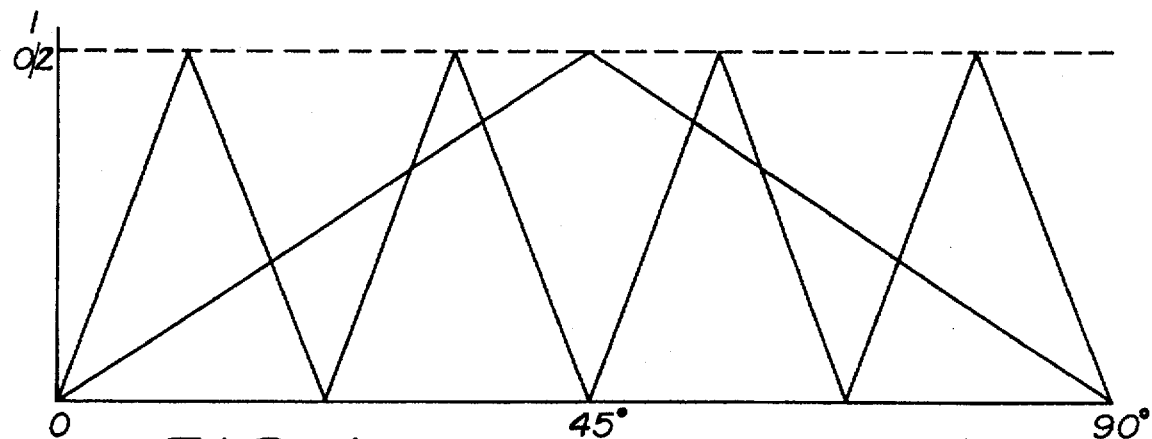
FIG. 4
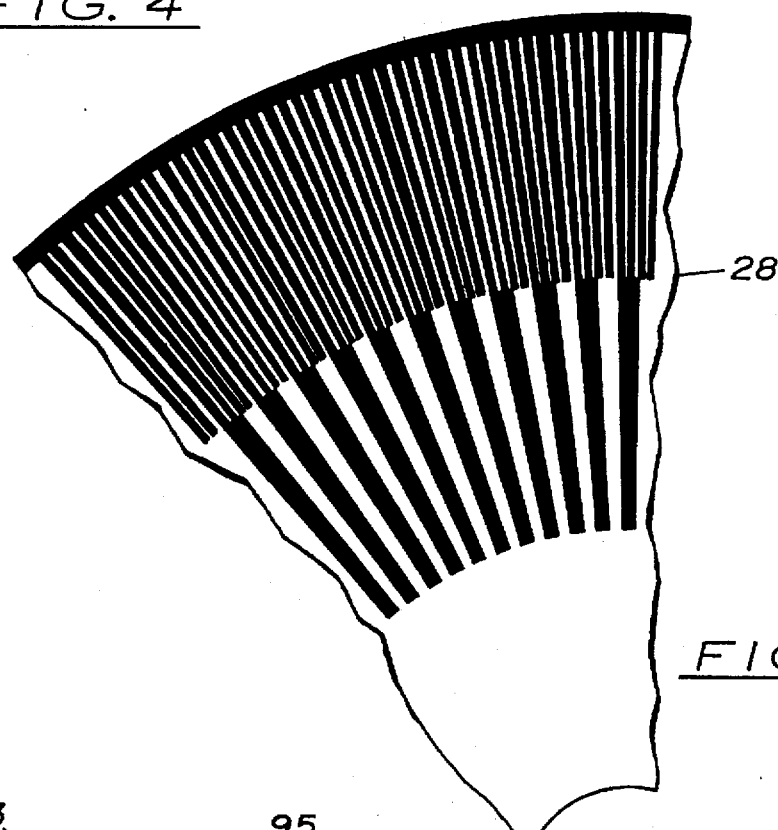
FIG. 5
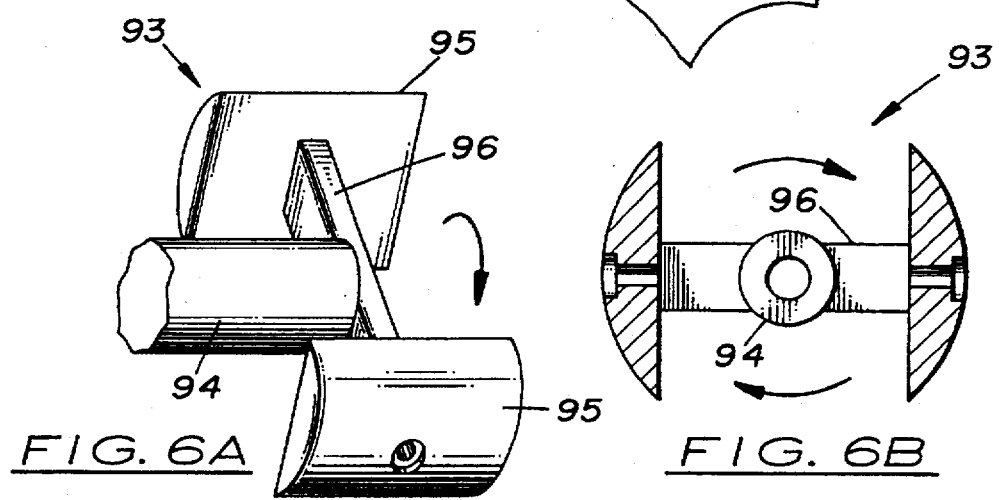
FIG. 6A
FIG. 6B

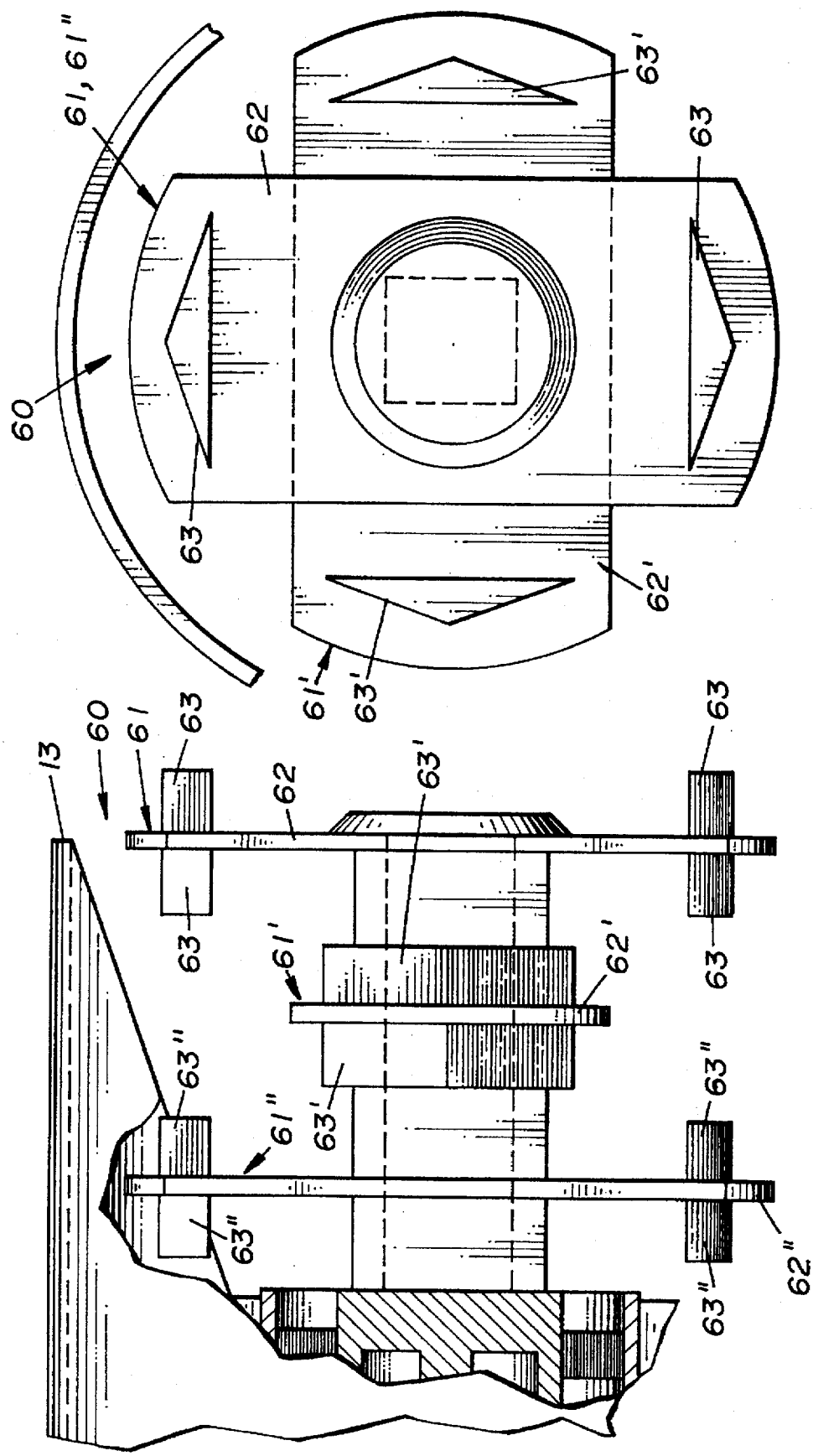

ROTATING CONSISTENCY TRANSMITTER IMPELLER AND METHOD

This is a continuation-in-part application of application, Ser. No. 08/525,945, filed on Sep. 8, 1995, now U.S. Pat. No. 5,600,058 and Ser. No. 08/624,982, filed on Mar. 29, 1996.

BACKGROUND OF THE INVENTION

1. Field of the Invention

The present invention is directed to a rotating torque measurement, and more specifically the use of a torque measurement to determine the consistency of a pulp slurry, the viscosity of a fuel oil, or in the mining industry, the concentration of a mining slurry in a grinding circuit.

2. Description of the Related Art

In the pulp and paper industry, the preparation and control of a pulp stream depends directly on the consistency of the moving pulp slurry. For example, the addition of bleaching additives, of retention aides, of various filler, starches and additives is all based on the consistency of pulp slurry. To date, the most accurate measurement of consistency is still based on a mechanical measurement of the shear forces exerted by the moving pulp stream on a sensing element.

Large boats and freighters are typically powered by large, oil-fired industrial boilers which use low grade, bunker fuel oils as the primary fuel. Bunker fuel oils are the residual grades of the petroleum distillation process and can have a very high viscosity. These types of fuel oils can only be injected into a boiler if they are pre-heated to sufficiently reduce their viscosity. The efficiency of the burning process directly depends on how well the bunker fuel oil can be made into a mist and how uniformly it can be injected into the boiler—both of these factors depend on the viscosity of the bunker fuel oil.

It has been found that both pulp consistency and fuel-oil viscosity can be determined by measuring the torque on the shaft of a rotating impeller. When consistency (or viscosity) increases, the shear forces on the rotating impeller increases and it takes a higher driving force (torque) to rotate the impeller. Commercial devices are available to affect such a measurement, such as a consistency transmitter type MEK-41 manufactured by BTG, a Swedish company, and a rotating viscosity meter manufactured by Brookfield, a USA company. The former device uses a sensing shaft concentrically mounted within a drive shaft. A shear force measuring element (impeller) is mounted on the exposed end of a "sensor shaft" which is positioned directly into the moving pulp stream or fuel-oil. The sensor shaft rotates with the same rotational velocity as the outer shaft and is loosely coupled thereto. The outer shaft provides the main rotational driving force to the impeller and shields the sensor shaft from the frictional forces between the drive shaft and the outer gasket material, which prevents the pulp slurry from entering the housing of the sensor unit.

In a typical implementation, the relative rotational motion between the inner sensor shaft and the outer drive shaft is sensed and a counter-torque is applied to the sensor shaft so that it will rotate at exactly the same rotational velocity as the drive shaft. This counter-torque is equal and opposite to the torque on the sensor shaft produced by the shear forces of the pulp slurry on the rotating impeller. In the prior art, this counter-torque is not based on an absolute measurement of torque, but rather on secondarily deduced factors as measured by an electronic transducer or a rotating pneumatic transducer operating on the flapper-nozzle principle.

While this technology has long been used and accepted by industry as the best and most accurate method of measuring consistency, it has two fatal draw-backs—lack of durability and reliability. A pulp slurry is very abrasive and corrosive. This means the gasket materials used to isolate the rotating shafts have a finite lifetime, measured in months, and when one of the gaskets fails, the entire device can fail catastrophically. Pulp slurry will then penetrate to the interior of the sensing housing and damage the sensitive elements. When a critical pulp consistency transmitter fails, the computerized process control loop goes out of control and the production line has to be shut down. For a large paper machine, the cost of such a forced shutdown is measured in the thousands of dollars per work shift. Therefore, it is important to provide a means to maintain and service a pulp consistency transmitter without having to shut down production.

Even though this invention makes specific reference to a pulp slurry and fuel oil, it should be understood that it also applies to a variety of other materials, such as natural and synthetic fibers like cotton, wool and kevlar fibers, as well as many other kinds of fluids, such as molasses in the crystallization process leading to the production of refined sugar.

SUMMARY OF THE INVENTION

It is, therefore, a general object of the present invention to provide an improved rotating consistency transmitter which is based on an absolute measurement of torque to allow for easy calibration both under laboratory as well as production conditions, and furthermore a device which incorporates certain features to make it very rugged for use in a corrosive and abrasive environment.

It is an object of the invention to provide such a transmitter which can be used, installed, serviced and dismounted without having to shut down a production line.

It is a further object of the invention to allow use of a transmitter which enables the measurement of torque to be linearized with increasing consistency.

It is a still further object of the invention to provide a method for accurately and predictably measuring the viscosity or consistency of a flowing multi-phase materials, such as a pulp slurry, in a pipeline.

These and other objects of the invention are met by providing a rotating consistency transmitter designed to measure the consistency, concentration or viscosity of a multi-phase material located in a container or flowing in a main pipeline by measuring the torque applied on a composite, torque detecting, rotating shaft. The rotating shaft comprises three concentrically aligned shafts—an outer drive shaft, a middle sensor shaft and an inner reference shaft. The three shafts are aligned and connected together so that when the outer drive shaft is rotated, the sensor shaft is rotated which, in turn, causes the reference shaft to rotate. In the preferred embodiment, the distal end of the outer drive shaft is attached to a rotating means capable of rotating the rotating shaft at a defined rotation speed. The proximal end of the reference shaft is connected to a force detecting means disposed inside the main pipeline. During operation when slurry is flowing through the main pipeline, rotation of the force detecting means is impeded thereby producing a twisting action on the sensor shaft. This twisting action produces a torque which is predictable and absolutely calibratable. The reference shaft, sensor shaft and drive shaft are isolated from the slurry. In one embodiment, the force detecting means has an intercepting surface located a fixed radial distance from the axis of the rotation which is perpendicular to the flow of the pulp slurry in the main pipeline and has a small, stream-line surface.

Attached to the transmitter is a torque detecting means capable of detecting the amount of torque applied to the sensor shaft. In the preferred embodiment, the amount of torque is determined by measuring the angular displacement between the distal and proximal ends of the sensor shaft. This angular displacement is measured by passing a focussed light beam across two closely aligned, transparent optical discs. Each optical disc has a plurality of opaque lines created thereon designed to prevent passage of light therethrough. One optical disc is attached to the distal end of the sensor shaft via the drive shaft while the other optical disc is attached to the distal end of the sensor shaft via the reference shaft. During operation, a focused beam of light is transmitted through the optical discs. The amount of light transmitted therethrough is a direct measurement of the torque acting on the sensor shaft.

As mentioned above, in one embodiment, the transmitter is attached to pipeline containing a flowing slurry. The transmitter is housed inside a carrying pipe which is selectively connected to the main pipeline via a positioning pipe. During assembly, the carrying pipe is inserted to the positioning pipe and attached thereto. An optional valve means is also provided which enables the positioning pipe to be selectively opened or closed thereby allowing the transmitter to be easily installed or removed from the main pipeline.

Using the above described transmitter, a method of measuring the consistency of a flowing liquid in a main pipeline is also provided.

BRIEF DESCRIPTION OF THE DRAWINGS

FIG. 4 is a diagram showing the relationship between the amount of light transmitted across the two optical disc and the amount of angular displacement.

FIG. 5 is a front plan view of an optical disc with a high density of opaque lines manufactured thereon.

FIG. 6A is a side elevational view of a two, semi-circular bladed impeller.

FIG. 6B is a front elevational view of the two, semi-circular bladed impeller shown in FIG. 6A.

FIG. 7A is a side elevational view of a three-bladed impeller.

FIG. 7B is a front elevational view of the three-bladed impeller shown in FIG. 7A.

DESCRIPTION OF THE PREFERRED EMBODIMENT(S)

The present invention in one embodiment finds preferred usage as a rotating consistency transmitter 2 in the pulp and paper industry. In a typical application in the bleach plant of a paper mill, the rotating consistency transmitter 2 is installed just prior to the chlorination stage, where the addition of chlorine to the pulp is critically controlled based on the amount of dry fiber flow. The amount of dry fiber flow is determined by the pulp flow velocity and the pulp consistency. The amount of chlorine added to the flowing pulp slurry determines how much the pulp gets bleached and also the residual amount of chlorine left after the bleaching stage. If the residual chlorine level is too high, this can lead to the formation of dioxin in the paper and also to the discharge of free chlorine into the atmosphere. Both conditions, of course, are undesirable.

Figure 1:
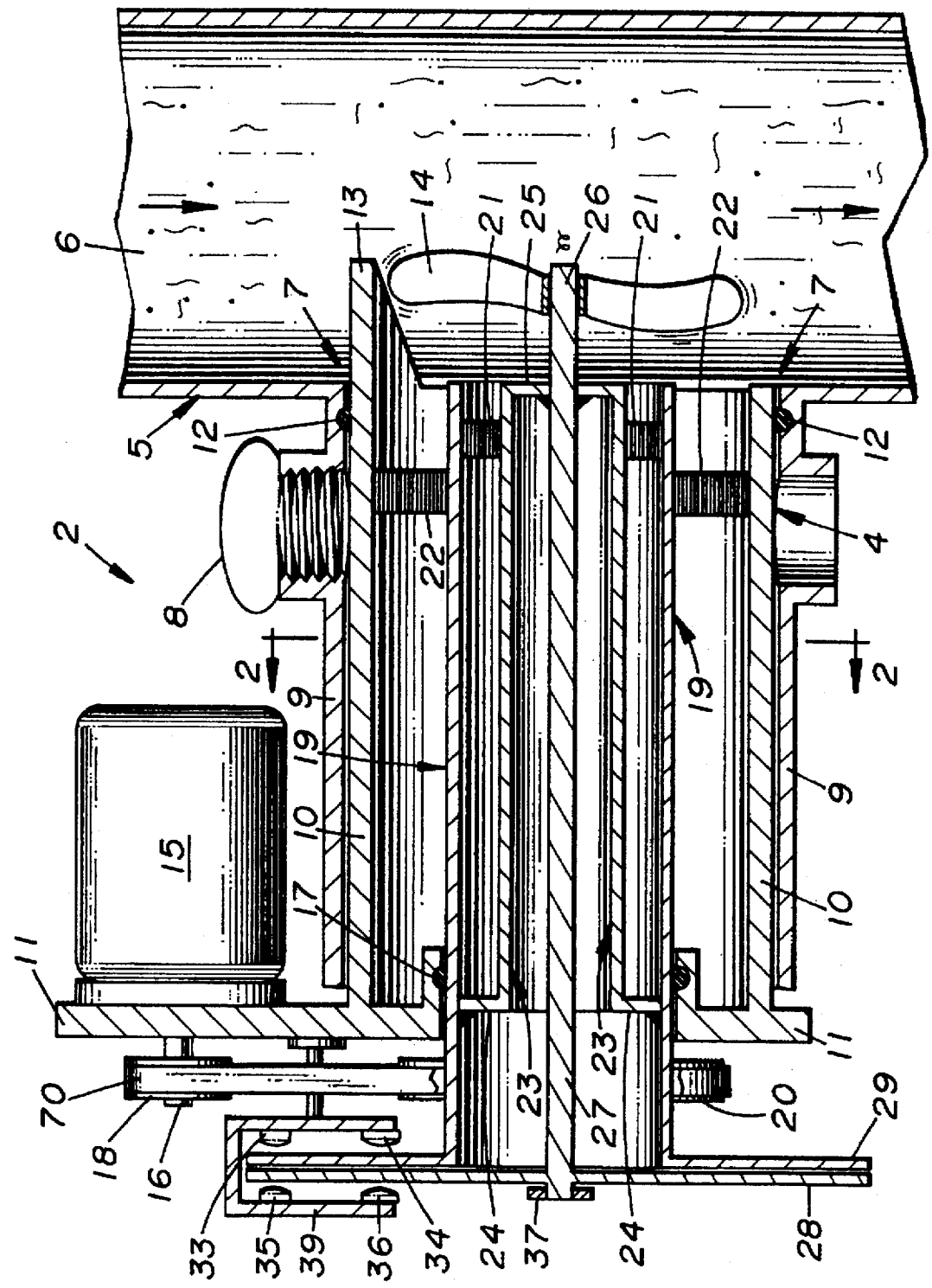
FIG. 1 is a sectional, side elevational view of the rotating consistency transmitter disclosed herein.

FIG. 1 shows the rotating consistency transmitter 2 comprising a carrying pipe 10 installed on the side of a main pipeline 5 which is transporting a pulp slurry 6 flowing in a downward direction. A side port 7 is formed on the side of the main pipeline 5 over which a positioning pipe 9 is attached. The positioning pipe 9 is hollow with an inner passageway, an outer distal opening, and an outer surface. The longitudinal axis of the positioning pipe 9 is aligned perpendicularly with the longitudinal axis of the main pipeline 5 and is designed to hold a hollow, longitudinally aligned, snug-fitting, carrying pipe 10. An optional gate valve 8 may be attached to the positioning pipe 9 which enables the positioning pipe 9 to be selectively opened or closed. As discussed further below, this feature enables the carrying pipe 10 to be selectively positioned or removed from the positioning pipe 9 for maintenance without requiring the fluid flow through the main pipeline 4 to be discontinued.

Attached to the distal end of the carrying pipe 10 is a drive plate 11 designed to hold the rotating means. The drive plate 11 partially extends into the central area of the carrying pipe 10 thereby acting as a support and an alignment surface for the drive shaft 19. First and second O-ring seals 12, 17 are disposed between the positioning pipe 9 and the carrying pipe 10 to create a water-tight seal therebetween. Formed on the proximal end of the carrying pipe 10 is a lip structure 13 which extends into the main pipeline 5 and is designed to protect the rotating impeller 14 from the flowing pulp slurry 6.

In the preferred embodiment, the rotating means is a fractional horsepower motor 15 mounted to the drive plate 11. The motor's drive shaft 16 has a motor drive shaft sprocket 18 mounted thereon which, in turn, rotates a belt 70 and powers the large diameter sprocket 20. The large diameter sprocket 20 is directly connected to the distal end of the drive shaft 19. When the motor 15 is operated, the belt 70 turns the sprocket 20 which, in turn, rotates the drive shaft 19.

Longitudinally aligned and positioned inside the carrying pipe 19 is a sensor shaft 23. The sensor shaft 23 has a flange surface 24 formed at the distal end thereof and a closed end surface 25. The flange surface 24 is welded to the inside surface of the carrying pipe 19. The configuration provides a barrier to keep the slurry 6 from entering the electronic area adjacent to the transmitter 2.

Longitudinally aligned and positioned inside the sensor shaft 23 is a reference shaft 27. The distal end of the reference shaft 27 is attached to the first optical disc 28 discussed further below. The proximal end of the reference shaft 27 is welded and extends through the end surface 25 on the sensor shaft 23. A force detecting means, such as an impeller 14, is mounted to the portion 26 of the reference shaft 27 that extends into the main pipeline 6.

A first gasketed rotating seal 21 is positioned between the inside surface of the drive shaft 19 and the outside surface of the sensor shaft 23. A second gasketed rotating seal 22 is positioned between the outside surface of the drive shaft 19 and the inside surface of the carrying pipe 10. When slurry 6 is flowing in the main pipeline 5, the first and second seals 21, 22 prevent slurry 6 from getting between the sensor shaft 23 and the drive shaft 19 and between the drive shaft 19 and the carrying pipe 10, respectively.

It is important to note that while the first gasketed rotating seal 21 is stationary with respect to both the drive shaft 19 and the sensor shaft 23, the second gasketed rotating seal 22 is positioned between two surfaces, which are rotating with respect to each other. The whole reason for introducing the drive shaft 19 is to prevent the frictional forces between the rotating drive shaft 19 and the stationary carrying pipe 10 from influencing the torque measurement across the sensor shaft 23. All frictional forces are taken up by the second seal 22 and are decoupled from the operation of the sensor shaft 23.

As mentioned above, the sensor shaft 23 is welded at its distal end to the inside surface of the drive shaft 19. During operation, shear forces acting on the impeller 14 causes a torque to act over the whole length of the sensor shaft 23, which produces a slight twisting action thereon. This twisting action is monitored by a reference shaft 27 which is welded to the inside surface of the proximal end of the sensor shaft 23. By fastening one first disc 28 to the distal end of the reference shaft 27 and a second disc 29 to the distal end of the drive shaft 19, respectively, one can directly observe the twist over the full length of the sensor shaft 23. In particular, it should be noted that the extent of the twisting action is a direct measure of the torque acting on the sensor shaft 23 and is an absolute quantity that can be directly related to the physical parameters of the sensor shaft 23, (i.e. the length, inner and outer diameters, material of construction, and its modules of rigidity).

The relationship between torque and twisting action can not only be expressed in concise mathematical terms but also by a straightforward empirical measurement, e.g. by holding one end of the sensor shaft 23 rigid, while applying a known amount of torque to the opposite end. This procedure can be easily repeated for different shafts to check the response of each shaft to a known amount of torque. In other words, if one holds the physical parameters of the sensor shaft 23 within tight specifications, one is able to measure the applied torque in absolute terms simply by measuring the amount of twisting action on the sensor shaft 23.

As shown in FIG. 1, the first and second optical discs 28, 29 are mounted to the ends of the reference shaft 27 and drive shaft 19, respectively. Two focussed laser diodes 33, 34 are radially mounted on a converted, U-shaped bracket 39 disposed over the peripheral edges of the discs 28, 29. The diodes 33, 34 are mounted on the bracket 39 along one side of the first and second optical discs 28, 29. Two respective light sensing photo diodes 35, 36 are mounted radially on the opposite side of the bracket 39 on the opposite side of the optical discs 28, 29. A mounting nut 37 is used to fasten the first optical disc 28 to the end of the reference shaft 27.

Figures 2, 3:
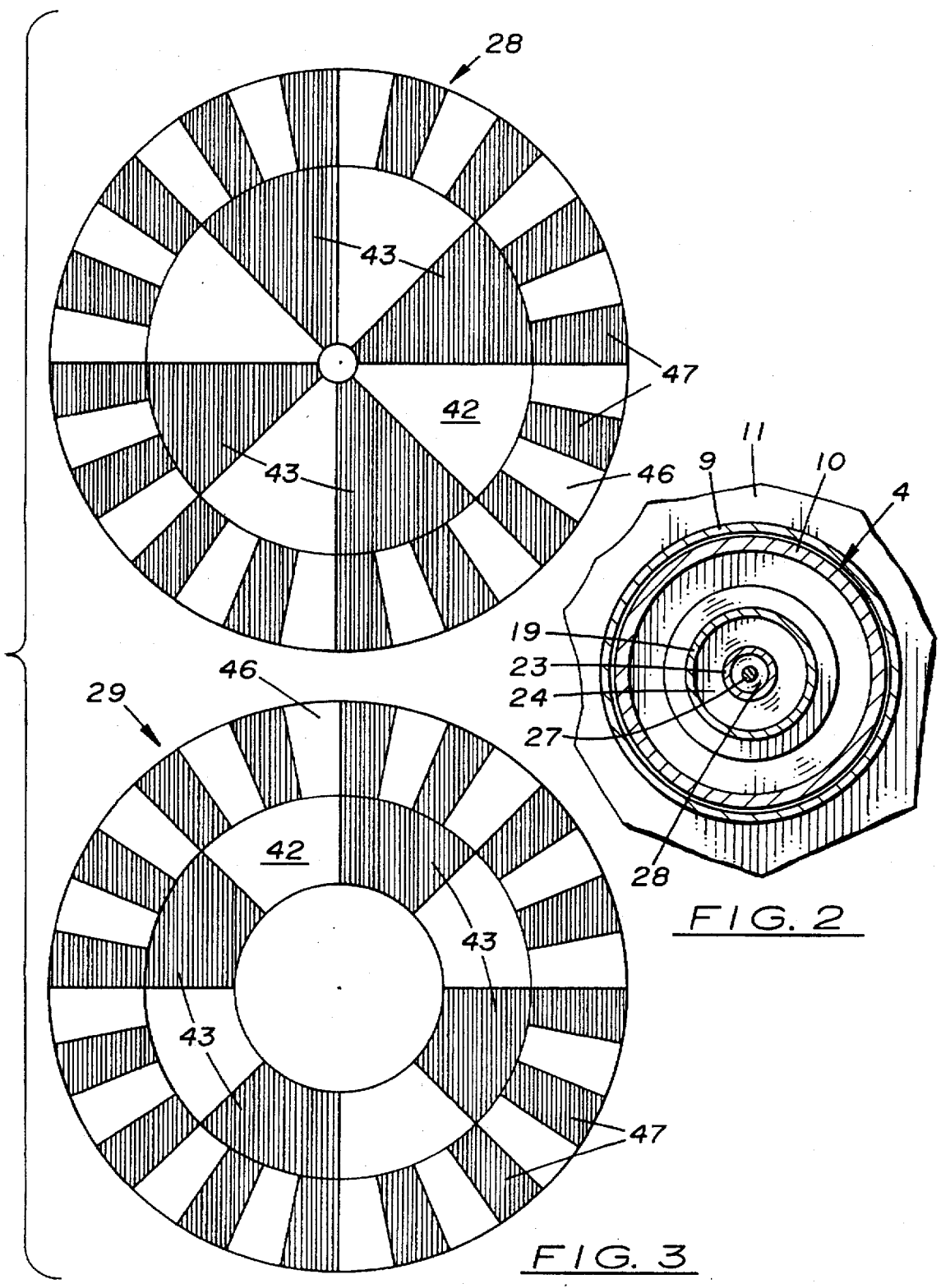
FIG. 2 is a sectional, front elevational view taken along Line 2—2 in FIG. 1.
FIG. 3 is a front plan view of the first and second discs.

FIG. 3 is a front elevation view of the two complementary first and second optical discs 28, 29, respectively. Optical discs 28, 29 are made of rigid, transparent material, such as glass or acrylic material with an inner circle area 42 having four opaque lines 43 and an outer circle area 46 having sixteen opaque lines 47. When initially installed on the transmitter 2, the positions of the optical discs 28, 29 are adjusted so that no light is transmitted across the two-disc interface. Then, when a torque is applied to the sensor shaft 23, the first and second optical discs 28, 29 are displaced with respect to the other, thereby allowing a certain amount of light to be transmitted in direct proportion to the amount of angular displacement of one disc with respect to the other. The maximum transmitted light intensity is 0.5 $I_o$, where $I_o$ is the full light output from the laser diode. This effect is linear up to a certain angular displacement, which depends on the number of lines on the disc's inner and outer circle areas 42, 46, respectively. Using this embodiment, the amount of light transmitted across the two optical discs, shown in FIG. 4, will be linear and will reach the maximum value (of $I_o/2$) for a displacement of 45° for the inner circle area 42 and 11.25° for the outer circle area 46. The corresponding amount of transmitted light is shown in FIG. 4 as a function of angular displacement. Obviously, by adding more opaque lines, one can increase the accuracy of this measurement.

With high resolution photo-etching techniques, it is possible to create many more lines on the optical discs as shown in FIG. 5. Let us assume a line density for the outer pattern of one line per degree or a full range of light transmission from 0 to $I_o/2$, over 0.5 degree of angular displacement.

Let us assume we use 360 optical lines per revolution, i.e. 1 line per 1° of angular displacement, then for an optical disc of 7.5 cm (3") diameter, the thickness of each line is equivalent to 0.5°, or about 33 micron in width. This means if we use a laser diode focussed down at the plane of the optical disc to produce a line measuring 33 microns (in width) by 2,000 microns (in length—aligned radially parallel to the lines) one can accurately measure the amount of rotational displacement (of one disc with respect to the other) to a resolution of better than 0.01°.

Let us further assume that the sensor shaft 23 is 20 inches long with an outer diameter of 12.7 mm (0.5 inches) and a wall thickness of 0.89 mm (0.035 inches). Then one can exactly calculate the amount of angular displacement "q" for a maximum amount of torque T as follows:

$q=(32T\ L)/(3.14(D_o^4-D_i^4)G)$, measured in radians, where:

T=torque=13 inch-pounds max

L=length of the sensor shaft=20 inches $D_o$=outer diameter of the sensor shaft=0.5 inches $D_i$=inner diameter of the sensor shaft=0.43 inches and, G=modules of rigidity of titanium=$5.6 \times 10^6$ psi.

With these parameters, using type II titanium alloy and a torque of 13 inch—pounds, the maximum amount of angular displacement is 0.034 radians, or about 2°. The beauty of this type of measurement is that it is an absolute measurement of torque and only depends on the dimensions and the material of the shaft, i.e. the modules of rigidity of the titanium shaft of the specific dimensions. The angular displacement of the sensor shaft 23 can be accurately calculated and even more accurately measured using static measuring techniques.

Another important advantage of this type of configuration is that (i) the structural integrity of the concentric shafts 19, 23, 27 is fully preserved, and (ii) there is no relative free motion between the outer and inner shafts 19, 27, respectively. These are two important benefits over the technology commonly used today, where the survivability of the whole system depends on the integrity of the first rotating seal 21 between the drive shaft 19 and the sensor shaft 23. In the prior art, a break in this seal 21 leads to the catastrophic failure of the whole system, whereas in the herein described invention, a break in the seal 21 merely allows some of the slurry 6 to leak between the sensor shaft 23 and the drive shaft 19. As there is no relative motion between the two shafts 19, 23, the effect of a leak has a negligible effect on the measurement.

Referring back to FIG. 1, it should be noted that the configuration of the positioning pipe 9 and the carrying pipe 10 is such that it allows the impeller 14 to be pulled back out of the slurry stream far enough to be extracted past the gate valve 8. Once the impeller 14 clears the gate valve 8, the gate valve 8 can be shut, thereby allowing the rotating consistency transmitter 2 to be removed from the positioning pipe 9 without having to shut down the production line. This is an important advantage in cases where it is important to maintain a constant production cycle.

The shape of the rotating impeller 14 determines how the impeller interacts with the fluid flow. If the impeller takes the form of a flat disc rotating about its common axis, it will preferentially measure the frictional forces on the flat surface of the disc. If it is instead a cylinder rotating within a larger, stationary, outer cylinder, it will preferentially measure the viscosity forces between the moving surface relative to the stationary surface.

When the impeller rotates within the pulp slurry, there are several forces acting on the impeller: (1) the yield stress forces that result when a moving object causes a separation (or break-up) of the fibers within an interlocking fiber network (also referred to as "coherent flocculation"); (2) the frictional forces caused by the moving fiber stream pressing against the flat surface of the impeller; and, (3) the turbulence forces caused by the wake of the moving impeller.

The Type (1) force is described in greater detail in *The Flocculation of Pulp Fibres, Papermaking Raw Materials*, R. J. Kerekes et al., Transactions of the 8th Fundamental Research Symposium held at Oxford, England, September, 1985, published by Mechanical Engineering Publ., Ltd. London, pps. 265–310. The authors describe the forces which act to give a fibre network its mechanical strength and how the tensile strength (or yield stress) of a fiber network is directly related to pulp consistency.

It should be noted that the other two forces of Type (2) and (3) are not only related to pulp consistency, but also to a number of variables, which, under process conditions, are typically not known or controlled.

The Type (2) force is like a classical frictional force and has the form: $F_f = \mu A N$, where $\mu$ is like the coefficient of friction, A is the surface area of the impeller, and N is the normal force per surface area and is related to the amount of pulp fibers carried within the pulp slurry. The coefficient of friction depends on a number of uncontrolled variables: (i) the viscosity of the carrying fluid (water) which depends on fluid temperature and hardness of it, i.e. the amount of mineral content; (ii) the smoothness of the surface structure of the impeller, and; (iii) the thickness of the water layer between the impeller surface and the moving pulp slurry, which acts as a lubricant.

The Type 3 force depends on (i) the fluid flow velocity, (ii) the size and rotational speed of the impeller, which determines the size of the wake left behind by the impeller blades, and (iii) the consistency of the pulp. When the pulp consistency drops below 1%, there are not enough fibers present in the flow to dampen the flow vortecies and turbulences set up behind the rotating impeller blades.

From these considerations, it is clear that for measuring pulp consistency, the best type of impeller is one that maximizes forces of Type 1 and minimizes forces of Types 2 and 3. In other words, it is best to have an impeller that has a front edge of maximum size with the smallest surface area. A simple piano wire positioned so that its major axis is perpendicular to the flow would be an idealized implementation of such a geometry. FIGS. 6A and 6B show a more realistic implementation of an impeller 93 for measuring pulp consistency, comprising two, semi-circular blades 95 mounted to a common support post 96, which, in turn, is fastened to shaft 94.

Figure 6C:
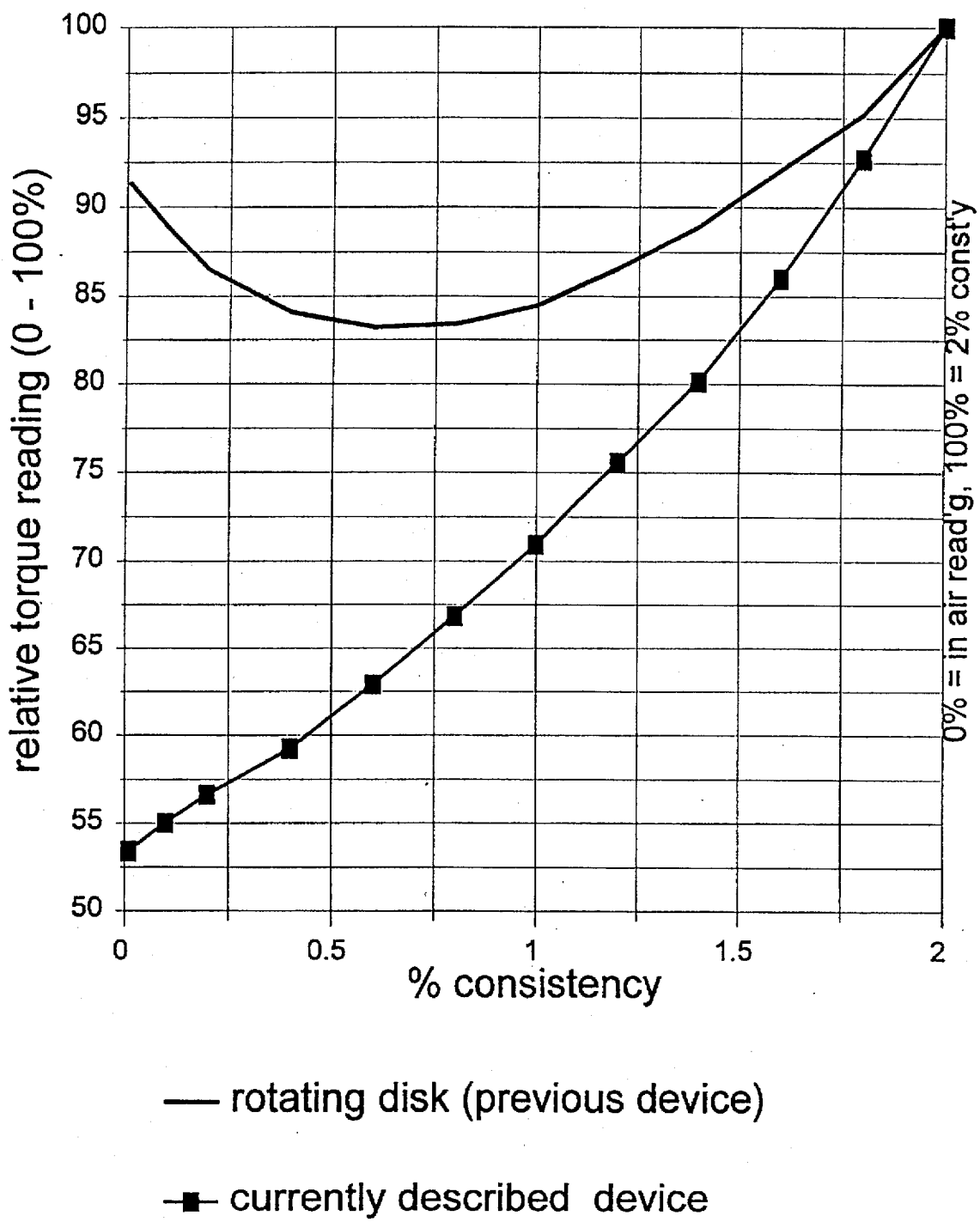
FIG. 6C is a graph measuring the relative torque reading and percent of consistency of the impeller shown in FIGS. 6A & 6B with a rotating disc impeller used in the prior art.
Figure 6D:
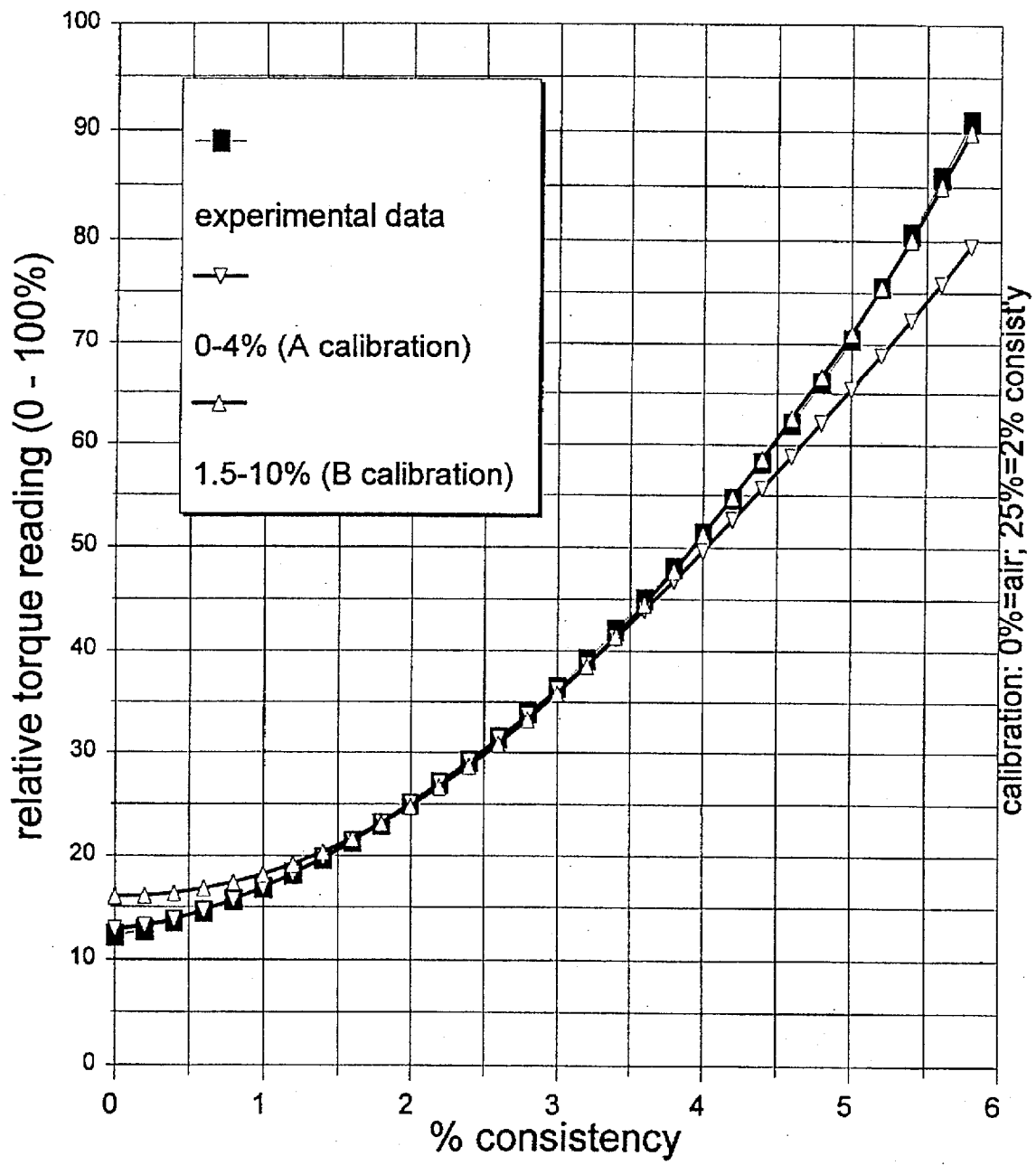
FIG. 6D is a graph measuring the torque versus percent of consistency at low and high consistencies.

FIGS. 6C & 6D are graphs which show the empirical results of a series of measurements conducted with both a conventional rotating impeller disc, as employed by a consistency transmitter type MEK-41, previously referred to, and the present device using an impeller as shown in FIGS. 6A & 6B, respectively. In FIG. 6C, the graph shows that the response of the former device levels off at about 1.0% in consistency, and that, below 0.5% consistency the torque reading actually increases with decreasing consistency. The explanation for this is that a rotating disc has a large surface area, which creates a certain amount of turbulence. This turbulence actually increases with decreasing consistency, as there are fewer fibers to damp the turbulence. This turbulence then acts as a brake on the rotating disc. In contrast, when an impeller of the type shown in FIGS. 6A & 6B is used, the torque reading continues to decrease with decreasing pulp consistency right down to 0.0% consistency. This indeed is a very significant finding.

In particular, it should be noted that the Type I force is directly proportional to the number of fibers, which are intercepted by the leading edge of the impeller causing the fiber network to be cut and dislodged. Most importantly, the work, $W_R$, done by the impeller, to cut the fiber network, does not depend on the rotational speed of the impeller, but only the total number of fibers $\Sigma N$ which have been intercepted by the impeller. This total number, $\Sigma N$, is given by the product: $W_R \sim \Sigma N \sim_\chi L\ DR$, where "$\chi$" is the consistency of the pulp (i.e. is proportional to the number of fibers in the pulp slurry), "L" is the length of the front edge of the impeller (perpendicular to the direction of motion), and "$D_R$" is the distance the impeller has traveled through the fiber network. With a rotating shaft, the distance $D_R$ is proportional to the incremental angular displacement $\theta$ between the two optical discs 28, 29. As long as the shaft rotates at a constant velocity, this angle $\theta$ is directly proportional to both the torque applied across the shaft and the work done by this torque.

During the time interval $T_M$ the shaft, rotating at an angular velocity $\Omega$, will have total angular displacement of $\alpha$, where: $\alpha = \Omega\ T_M$.

If $\Omega$ changes (increases), then one has to modify (reduce) the time interval $T_M$ to maintain a constant angle $\alpha$. This can simply be done by measuring the time interval $\Delta T$ between the successive light pulses received across the discs 28, 29 compared to a reference time interval $T_{ref}$ obtained at a constant reference speed. One can obtain a speed compensated measured angular displacement $\theta_c$ as follows: $\theta_c = \theta \Delta T / T_{ref}$ When the rotational speed increases, the sensor element will intercept more fibers; this means the torque reading will be higher. However with higher speed, the time interval between successive light pulses will be less in direct relationship to the rotational speed. By using the speed corrected angular displacement value $\theta_c$, one can measure the work done by the impeller.

If one uses a stationary knife edge to intercept a moving pulp stream, the effect will essentially be the same as for a rotating impeller. In this case, the work $W_s$ done by the knife edge in slicing through the moving slurry is again the product of $W_s \sim \Sigma N \sim \chi L\, D_s$, where again "$\chi$" is the consistency of the pulp (i.e. is proportional to the number of fibers in the pulp slurry), "L" is the length of the front edge of the stationary knife (perpendicular to the direction of motion) and "$D_s$" is the distance the knife has sliced through the fiber network. In this case the distance is equal to: $D_s = VT_M$, where "V" is the velocity of the pulp flow, and "$T_M$" is the measuring time interval. If the velocity changes, one can maintain a constant "$D_S$" by adjusting the corresponding measuring time interval "$T_M$". Using this method, one can measure the pulp consistency simply by keeping "L" and "$D_S$" constant and by measuring the total work (per unit distance "$D_S$") done by a stationary knife edge intercepting the pulp stream. This work is direcely proportional to the strain on the front edge of the knife integrated over the (velocity corrected) measuring time interval "$T_M$". The strain on the stationary knife can be measured by using conventional strain gauge technology.

There are numerous mechanical measuring devices available today for measuring pulp consistency. They are basically split into two types: (i) rotating devices, which measure the torque on the drive shaft, and (ii) "hockey-stick" devices, which are stationary devices deposed into the moving pulp slurry. The MEK-41, made by BTG, and the rotating consistency transmitter made by DeZurik are examples of the former. The PULP-EL blade made by Valmet, the CONS-Mark 100 made by Conmark Instruments are examples of the latter. All of these devices basically have a large surface area parallel to the pulp flow, which measures the "apparent viscosity", the force exerted by the moving pulp slurry against the flat surface. In all of these devices there is a relatively small front cutting edge to intercept the fiber network.

As stated before, it is important to select a sensor geometry, which maximizes the influence of Type I forces, while minimizing the influence of Type II and Type III forces. This basically means that the sensor has to have a long cutting edge "L", with a minimized surface "S". Expressed as an (inverse) ratio "S/L", this means that "S/L" (expressed in length units of "inches") should be as small as possible. The ratio "S/L" is given below in Table I for several different kinds of mechanical consistency sensors, commercially available:

TABLE I

| Type | Company | Name of Device | S/L (in.) |
|---|---|---|---|
| Rotating | BTG | MEK-41 with Type A sensing element | 10 |
|  |  | With type B sensing element | 10 |
|  |  | With type C sensing element | 12.5 |
| Rotating | DeZurik | Rotating consistency device With 10.5" diameter disc | >20 |
| Stationary | Valmet | Pulp-EL | 12 |
| Stationary | Conmark | Con Mark 100 Instrum. | 12 |
| Stationary | DeZurik | AccuTrax | >20 |
| Stationary | TECO | TMC-6000 | 3.14* |
| Rotating |  | Present device with impeller shown in FIGS. 6A & 6B | 2 |

(*This device measures the forces on the rod-like structure placed perpendicular to the pulp stream. Because the structure is not streamlined it will create a lot of front surface friction and flow turbulence.)

Table I shows that the present device has a S/L ratio of 2 inches, which is about 5 times smaller than most of the other commercial products. This means that Type I forces are 5 times greater than Type II forces. Furthermore, whereas none of the above commercial devices is able to measure consistency below 1%, the present device is able to measure consistency reliably down to 0.0% consistency. The reason for this is that, at the lower consistencies, the water turbulence, caused by the conventional type of sensing element, is too high and will swamp out the small force readings due to the fibers.

In the case of the TMC-6000 probe, the probe does have a smaller "S/L" ratio of 3.14, but it is not streamlined and the water turbulence and front surface friction again are larger than the Type I forces.

In the FIG. 6D, the graph shows the experimental results on softwood bleached Kraft (SBK) pulp [shown as dark squares]. FIG. 6C shows two simple calibration curves "A" and "B", which are used to linearize the measured curve. At low consistencies, in the range from 0 to 4% consistency, the relative torque reading is best described by calibration curve "A", which has the simple form: calibration curve $A \sim a_1 + b_1 * \chi^{1.6}$, where $a_1$ and $b_1$ are constants and $\chi$ is the pulp consistency.

At higher consistencies, in the range from 1.5 to 10% consistency, the relative torque reading is best described by calibration curve "B", which has the simple form: calibration curve $B \sim a_h + b_h * \chi^{2.0}$, where "$a_h$" and "$b_h$" again are constants and "$\chi$" is the pulp consistency. The difference between curves "A" and "B" is that they have different power functions. At low consistency the relationship between torque and consistency is best described by a function with the power of 1.6, whereas at higher consistencies, the relationship is that of a power function of 2.0. This can be best understood by the fact that at lower consistencies, the fibers have not yet formed a fiber network, and are hitting against the sensing blade as individual fibers. In that case, the torque is best described by how many fibers there are per linear dimension. At higher consistencies, the fibers are part of a fiber network, where each fiber is held in place by all of the surrounding fibers in the volume surrounding each fiber, i.e. the relationship goes as a higher power function of consistency. It should be noted that the power function will vary to some degree with the type of fibers that are being measured. If the fibers are long and thin, they will make up a stronger fiber network, i.e. the power function will be higher, as compared to a fiber slurry that consists of shorter fibers. Empirically it has been determined that the power factor can vary over the following range:

For calibration curve A: 1.2<power factor<2.0.

for calibration curve B: 1.5<power factor<3.0.

In order to get a linearized output reading expressed in "%-pulp consistency", it is necessary to invert the above two calibration functions, to solve for the variable $\chi$. This then leads to 2 equations expressed in terms of torque (the measured variable) $\tau$:

for low consistency: $\chi = [(\tau - a_1)/b_1]^{pfA}$, where $0.50 < pfA < 0.83$;

for higher consistencies: $\chi = [(\tau - a_h)/b_h]^{pfB}$, where $0.33 < pfB < 0.66$.

These two equations linearize the output to provide a calibrated output reading of pulp consistency. It should be noted that in order to come up with a single calibration curve to cover the entire range of the instrument, from 0.0 to 10% in consistency, it would be necessary to use a polynomial function of the type: $\tau = a_1 + b_1 \chi + c_1 \chi^2 + d_1 \chi^3$, where $a_1$, $b_1$, $c_1$ and $d_1$ again are constants. In this case, it is not very easy to invert this equation to linearize the output reading in terms of the measured variable $\tau$.

From these discussions it is clear that the designers of the presently available mechanical consistency transmitters have not made a distinction between the three types of forces and have not recognized the importance of maximizing Type I forces, while minimizing Type II and Type III forces. Furthermore, nobody has made a distinction between the forces at low consistency and those at higher consistency. The impeller geometry shown in FIGS. 6A & 6B seeks to optimize Type I forces while minimizing the other influences. It should also be recognized that the impeller shown in FIGS. 6A & 6B may be further modified by curving (or placing at an angle) the front (leading edge) cutting surface to prevent fibers and other debris from adhering to the front edge of this surface.

From the results shown in FIG. 6C, one can draw one more important conclusion—there is a very basic difference between a disc-shaped sensing element, as used by current devices, and a cutting blade, as shown in FIGS. 6A & 6B. With a conventional star-shaped rotating disc, the surface intercepting the pulp flow has various radial distances, and hence has also various rotational velocities with respect to the pulp flow. This creates excessive vortex formations over the surface of the rotor, which act as a brake on the rotating sensing element, as shown in FIG. 6C. It also means that there is no clear relationship between the work performed by the sensing blade and the angular distance "$D_R$", which is velocity dependent. The only way to maintain a constant relationship is to maintain a constant angular velocity, which can only be achieved by maintaining a constant rotational speed, by using an expensive, synchronously driven, three phase motor.

In the presently described device, the intercepting surface is at a fixed radial distance and has a small, stream-lined surface. This minimizes vortex formation and also establishes a clear relationship between the work done by the impeller and the angular displacement. As long as one always measures the work over a constant angular displacement, one can use any cheap, non-synchronously, driven motor.

Kerekes et. al. (Ref.: Motion of Pulp Fibre Suspensions in Rotary Devices, C. P. J Bennington, R. J. Kerekes, and J. R. Grace, *The Canadian Journal of Chemical Engineering*, Vol. 69, February 1991, page 251–258) have shown that, to a first order approximation the torque resulting from the shear forces of a pulp slurry acting on a rotating impeller has a relationship that is somewhere between a square law and a cube law with consistency. This means that for higher consistencies, above 8%, the shear forces are so high that even with a relatively small impeller, with a 3.5" diameter, the torque can easily be measured. However, at smaller consistencies, below 3%, the shear forces are relatively small. With the above-described gate-valve 8 configuration, the maximum diameter of the impeller is determined by the maximum opening size of the gate valve 8.

FIGS. 7A & 7B show another embodiment of the force detecting means including a stacked, three bladed impeller 60. The impeller 60 has three blades 61, 61', and 61" stacked side by side each other with each successive impeller being rotated 90°, so that the slurry can flow freely between the neighboring blades. Each blade 61, 61', 61" comprises a thin, rectangular-shaped plate 62, 62' 62", respectively, with two pairs of separating wings 63, 63', 63" at each side of the plate at opposite ends. A square-shaped mounting hole is also provided which enables the impeller 60 to fit onto a complementary shaped reference shaft.

FIG. 1 shows an optional flow breaker lip structure 13 located at the end of the carrying pipe 10. This lip structure 13 breaks up the pulp flow in front of the impeller(s) and reduces the influence of the velocity of the pulp slurry 6. It also protects the impeller 14 from the impact of dried pulp slugs, which can destructively impact anything positioned inside the flow line. The size and shape of this lip structure 13 depends on the consistency of the pulp flow and the number of impeller blades. In some instances, it may in fact be preferable to mount the lip structure 13 some distance upstream from the impeller 14 in order to minimize the amount of dewatering of the pulp prior to the measuring region, which could give erroneous readings of consistency.

According to the *Handbook of Chemistry and Physics* (published by: The Chemical Rubber Publishing Co., 1961, page 2194) the viscosity of a substance is defined as "the tangential force per unit area of either of two horizontal planes at unit distance apart, one of which is fixed, while the other moves with unit velocity, the space being filled with the substance."

Figure 8:
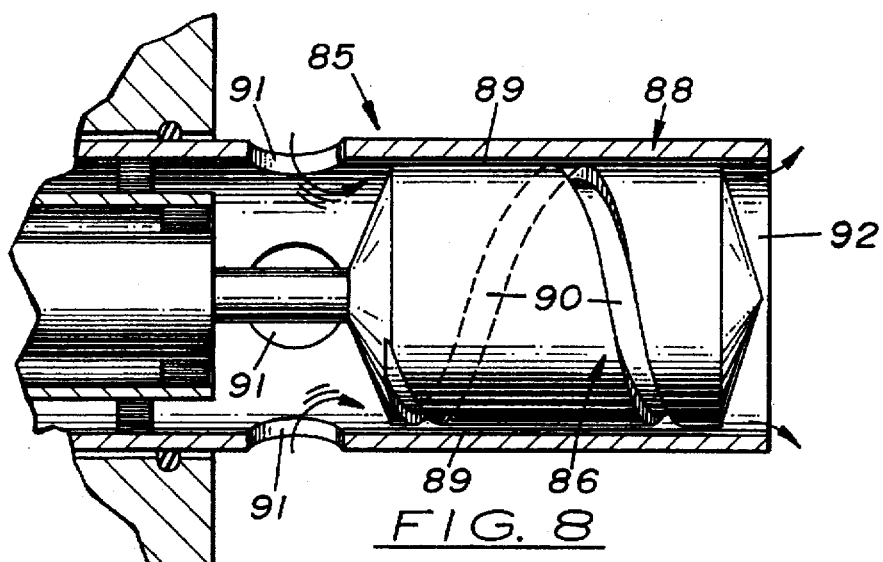
FIG. 8 is a side elevational view of the rotary viscosimeter.

FIG. 8 shows still another embodiment of the force detecting means comprising a rotary viscosimeter 85. The viscosimeter 85 is similar to the viscosimeter disclosed by Winter in U.S. Pat. No. 4,077,251 having an inner cylindrical shape 86 which rotates within a larger outside cylinder 88. The gap 89 between the cylindrical shape 86 and the cylinder 88 is constant. The cylindrical shape 86 and the cylinder 88 define the two horizontal planes, and the torque which has to be applied to the inner rotating cylinder 86 defines the tangential force referred to in the above-referenced definition. A narrow screw band 90 is attached to the outer surface of the cylindrical shape 86 to draw fluid in through holes 91 located in the outer cylinder 88 along the gap 89 and out through the opening 92 on the cylinder 88 back into the primary flow. This ensures that the fluid substance within the cylindrical shape 86 and the cylinder 88 is continually being exchanged.

To linearize the measurement of consistencies ($C_y$) over a wide range of readings, it is necessary to apply a fractional root function to the raw torque reading (t), as follows: $C_y = a \, t^{-1/b}$, where "a" is a constant and "b" is a factor between 2 and 3. In the simplest form, "b" is 2, and the consistency is simply obtained by using a square root conversion circuit using an 'integrated circuit multiplier' type AD532 from Analog Devices, or similar (ref.: 1992 Special Linear Reference Manual, published by Analog Devices). The same device can also be used to obtain a cube root function or various combinations in between.

Figure 9:
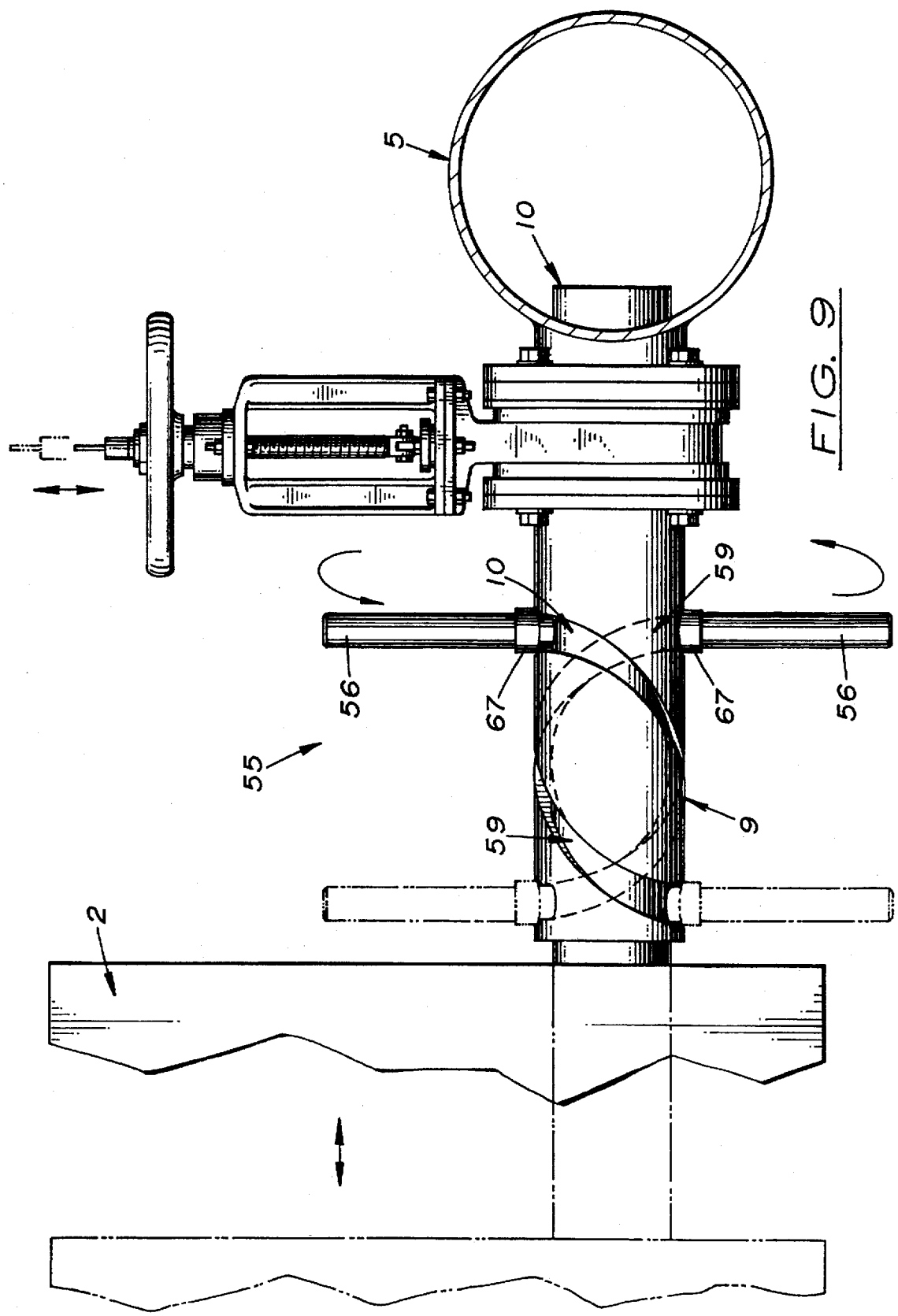
FIG. 9 is a side elevational view of the extraction device which allows the impeller to be extracted past the gate valve.

FIG. 9 shows a screw-feed leveraging device 55 which allows the rotating consistency transmitter 2 to be forcible and safely removed from the in-line position in the positioning pipe 9. It should be noted that some main pipelines operate up to a pressure of 10 bar, i.e. 150 psi. At 3.5 inch diameter, the cross-sectional area of such pipelines is 9.62 square inches, which, at 10 bar, results in a total pressure of 1,440 pounds of force. Removing the rotating consistency transmitter 2 from the main pipeline can be difficult and hazardous.

The leveraging device 55 includes two, long handles 56, threadingly attached at one end to the opposite sides of the carrying pipe 10. The two handles 56 extend through a spiral cut-out 59 formed in the positioning pipe 9. During use, the carrying pipe 10 is moved longitudinally inside the positioning pipe 9 by turning the handles 56, thereby causing them to follow the cut-out 59. The location, pitch and length of the cut-out 59 is sufficient so that the one rotation of the handles 56 causes the carrying pipe 10 to move a sufficient distance inside the positioning pipe 9 so that the impeller end of the carrying pipe 10 clears the gate valve 8.

Figure 10:
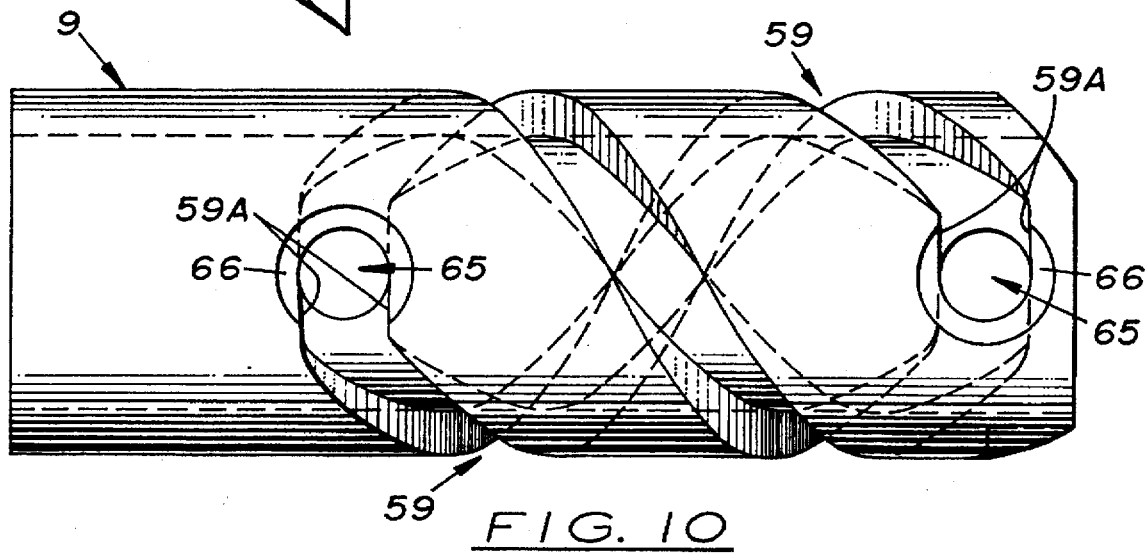
FIG. 10 is a side elevational view of the positioning pipe shown in FIG. 9 detached from the main pipeline with the carrying pipe removed.

The positioning pipe 9 is shown in greater detail in FIG. 10. The spiral cutout 59 has flat surfaces 59A manufactured on the distal and proximal ends thereof which act to prevent longitudinal movement of the carrying pipe 10 within the positioning pipe 9 when the handles 56 are being manually locked or unlocked in position on the positioning pipe 9.

Figure 11:
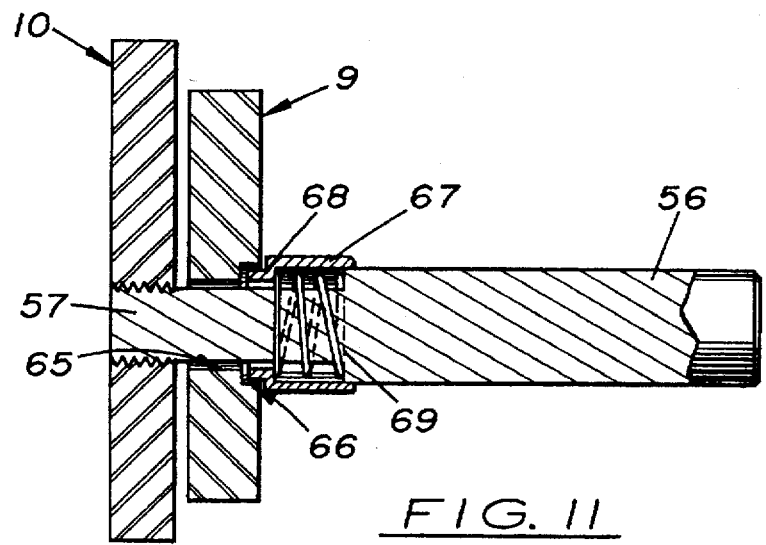
FIG. 11 is a sectional, side elevational view of the leverage insertion assembly showing the placement of the carrying pipe, positioning pipe, and the handle.

A locking means is provided for locking the handle 56 in position on the positioning pipe 9. In the embodiment shown in FIGS. 10 and 11, the locking means includes an outer bushing 67 that has a lower neck 68 that engages a recess surface 66 formed at each distal and proximal end of the spiral cut-out 59. A biasing spring 69 disposed between the bushing 67 and the handle 56 forces the bushing 67 inward to engage the recess surface 66 when handle 56 is properly aligned over the opening 65. When each bushing 67 is moved outward to disengage the recess surfaces 66, the handles 56 may be manually turned to follow the spiral cut-out 59. The end surfaces 59A formed on the spiral cutout 59 temporarily hold the carrying pipe 10 in position in the positioning pipe 9 so that the operator may be properly positioned for removing or attaching the carrying pipe 10 in the positioning pipe 9.

In this manner, the handles 56 are used both as a leveraging tool and as positioning tool to move the carrying pipe 10 inside the positioning pipe 9. When the carrying pipe 10 is longitudinally moved inside the positioning pipe 9 so that the impeller end of the carrying pipe 10 clears the gate valve 8, the handle on the gate valve 8 may be turned to close the gate value 8 thereby preventing slurry from flowing through the positioning pipe 9. The carrying pipe 10 and hence, the rotating consistency transmitter, can then be removed from the positioning pipe 9.

It should be recognized, by those skilled in the art, that the leveraging device 55 is a novel way of inserting any element used to measure or sample the material in an in-line pressurized flow, and has uses and applications that are not solely restricted to the herein described measuring technique. This particular leveraging device 55 represents a fifth generation design that has been evolved over a period of fifteen years by the current inventors in an on-going effort to provide a simpler and safer way of inserting a device into a fully pressurized line. Other possible uses for such a leveraging device 55 are the insertion of an optical measuring head to determine brightness, concentration, turbidity, index of refraction of a process fluid, as well as to allow for extraction of a sample of the fluid for purposes of laboratory testing.

Using the above described transmitter 2, a method for measuring the consistency of a flowing liquid in a pipeline is also disclosed. The method comprises the following steps:

a. selecting a consistency transmitter disclosed herein;

b. locating the consistency transmitter so that the force detecting means is placed into the slurry;

c. rotating said force detecting means in said slurry;

d. measuring the amount of light transmitted across said first and second optical discs;

e. determining the amount of torque across said sensor shaft based on the amount of light transmitted across said first and second optical discs; and, f. calculating the consistency of said slurry based on the torque measurement on said sensor shaft.

In compliance with the statute, the invention, described herein, has been described in language more or less specific as to structural features. It should be understood, however, the invention is not limited to the specific features shown, since the means and construction shown comprised only the preferred embodiments for putting the invention into effect. The invention is, therefore, claimed in any of its forms or modifications within the legitimate and valid scope of the amended claims, appropriately interpreted in accordance with the doctrine of equivalents.

I claim:

1. A force detecting means for a rotating consistency transmitter capable of determining the consistency of a flowing pulp slurry, said force detecting means including at least two semi-circular blades mounted on a support means, each said blade having an intercepting surface fixed at a radial distance from the axis of rotation thereof.

2. A force detecting means, as recited in claim 1, which has a leading edge of length L and a surface area S, so that the ratio S/L is less than 8 inches.

3. A method of measuring the consistency of a flowing pulp slurry by measuring the work done by forces acting on a detection means over a speed compensated measured angular displacement on said force detecting means.

4. A method of measuring the consistency of a flowing pulp slurry, as recited in claim 3, wherein the amount of work done by forces acting on a detecting means is linearized over the range for 0 to 4% consistency, using the functional relationship: $\chi=[(\tau-a_1)/b_1]^{pfA}$, where $\tau$ is the amount of torque, $a_1$ and $b_1$ are constants, and pfA is less than 0.83 but greater than 0.50.

5. A method of measuring the consistency of a flowing pulp slurry, as recited in claim 3, wherein the amount of work done by forces acting on a detecting means. is linearized over the range from 1.5 to 10% consistency using the functional relationship: $\chi=[(\tau-a_h)/b_h]^{pfB}$, where $\tau$ is the amount of torque, $a_h$ and $b_h$ are constants, and pfB is less than 0.66 but greater than 0.33.

* * * * *

UNITED STATES PATENT AND TRADEMARK OFFICE
Certificate

Patent No. 5,684,247            Patented: November 4, 1997

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Ekhard Preikschat, Bellevue, Washington; and Robert Hilker, Kirkland, Washington.

Signed and Sealed this Twelth Day of March 2002.

HEZRON E. WILLIAMS
*Supervisory Patent Examiner*
Art Unit 2856